United States Patent [19]

Bayers

[11] 4,392,495
[45] Jul. 12, 1983

[54] APPARATUS FOR AND METHOD OF SUTURING TISSUE

[76] Inventor: Jon. H. Bayers, 2935 Bechelli Ln. Suite C, Redding, Calif. 96001

[21] Appl. No.: 298,030

[22] Filed: Aug. 31, 1981

[51] Int. Cl.³ .............................................. A61B 17/04
[52] U.S. Cl. ................................ 128/334 R; 128/1 R
[58] Field of Search .................... 128/334, 335–339, 128/1 R, 325–327, 303 R

[56] References Cited

U.S. PATENT DOCUMENTS 4,133,339  1/1979  Nascund ............................. 128/339
4,140,125  2/1979  Smith .................................. 128/325

Primary Examiner—Stephen C. Pellegrino

[57] ABSTRACT

A method of suturing tissue including passing a flexible, tubular suture through the tissue. The tissue collapses the tubular suture but is reopened when a second suture is introduced through the tubular suture. A tissue may be severed with the first, flexible, tubular suture before the introduction of the second suture. The second suture is fastened in relation to the tissue to complete the suturing method.

7 Claims, 4 Drawing Figures

APPARATUS FOR AND METHOD OF SUTURING TISSUE

BACKGROUND OF THE INVENTION

The present invention relates to a novel suture apparatus and method of suturing tissue.

Many surgical procedures require the use of sutures to refasten severed tissue. The object of suturing is to reattach severed portions of the tissue in as close proximity as possible to the original position. Where the tissue has involuntarily severed the surgeon must surmise a place of attachment of the severed parts of the tissue. Where the cutting of the tissue results from a surgical procedure, the physician is in a much better position to make this determination. However, accurate suturing of tissue in this manner is often a difficult task even for the most skilled surgeon. This problem is especially acute in delicate surgical procedure such as eye surgery.

It would be a great advance in the medical art if a device and/or method were obtained permitting accurate suturing of severed tissue.

SUMMARY OF THE INVENTION

In accordance with the present invention a novel and useful apparatus for a method of suturing tissue is provided.

The apparatus of the present invention employs a first, flexible, severable, tubular suture which is capable of passing through the tissue. The first, flexible suture may be drawn through the tissue with a conventional suture needle. The first, flexible, tubular suture may also possess the capability of being collapsible within the tissue.

A flexible needle is also provided which is capable of passing through the first, flexible, tubular suture which may or may not be collapsed. The flexible needle would include a blunted tip to prevent stoppage of the same through the first, flexible, tubular suture by catching or contacting the side of the same.

It may be also shown that a novel method for suturing tissue is included in the present invention. The method includes the step of passing a first, flexible, tubular suture through the tissue or portions of the tissue which are adjacent one another. The first, flexible, tubular suture may collapse upon itself under the pressure of the tissue body. At this point, the surgeon severs the tissue at the appropriate place. The first, flexible, tubular suture is also severed with this surgical step leaving two ends visible within the incision. The collapsed portion of the first, flexible, tubular suture is opened by the introduction of a second suture through the first, opened, flexible, tubular suture. A second suture is introduced by the use of a flexible needle having a blunted tip. After introduction of the second suture through the severed tissue portions, the severed parts of the first, flexible suture are removed from the tissue by sliding the same over the second suture. It should be apparent that a third, flexible, tubular suture may be placed adjacent the first, flexible, tubular suture such that the second suture may be passed through the first and third, flexible, tubular sutures respectively. Moreover, a plurality of flexible tubular sutures may be placed adjacent one another along the route of the incision such that the second suture may take the form of a continuous suture.

It may be apparent that a novel and useful apparatus for a method of suturing tissue has been described.

It is therefore an object of the present invention to provide an apparatus for a method of suturing tissue which accurately allows the re-approximation of the severed portions of tissue resulting from a surgical incision.

It is another object of the present invention to provide an apparatus for a method of suturing tissue which is safely and easily performed by a surgeon.

It is yet another object of the present invention to provide an apparatus for a method of suturing tissue which is especially useful in eye surgery.

The invention possesses other objects and advantages, especially as concerns particular features and characteristics thereof, which will become apparent as the specification continues.

Figure 1:
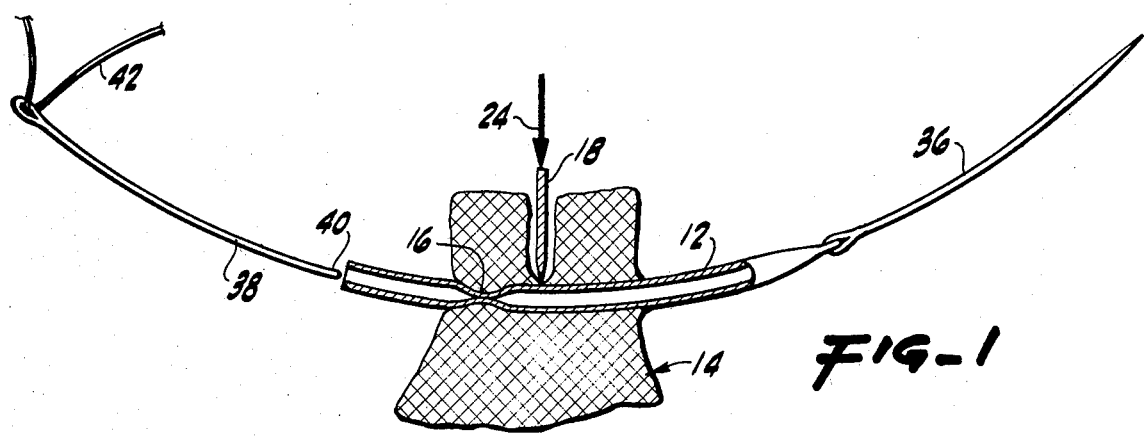
FIG. 1 is a broken sectional view showing the apparatus and method of the present invention in operation.

For a better understanding of the invention, reference is made to the following detailed description which should be referenced to the hereinabove described drawings.

DESCRIPTION OF THE PREFERRED EMBODIMENTS

Various aspects of the present invention will evolve from the following detailed description of the preferred embodiments thereof which should be taken in conjunction with the hereinabove described drawings.

The invention as a whole is represented in the drawings by reference character 10. The apparatus 10 includes a first suture 12 which possesses flexibility and is capable of passing through tissue 14, FIG. 1. Tissue 14 may collapse suture 12 as shown in tissue portion 16, FIG. 1. Suture 12 may be constructed of any nonreactive flexible material such as silicon, and other polymeric compounds known in the art. First suture 12 is also severable by surgical knife or scalpel 18. It should be noted that surgical knife 18 may be any known device for severing tissue 14 including laser beams and the like.

Figure 2:
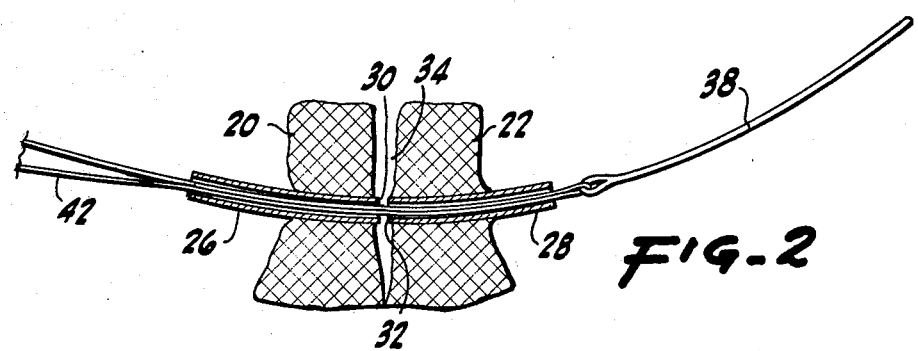
FIG. 2 is a broken sectional view showing the apparatus and method of the present invention in operation.

Turning to FIG. 2, it may be seen that tissue 14 has been cut into two portions 20 and 22 by the force of surgical knife 18 along line of force 24, FIG. 1. Tubular suture 14 has also been severed into portions 26 and 28. Edges 30 and 32 of suture portions 26 and 28 respectively are visible within crevice 34 between portions 22 and 24 of tissue 14. The surgeon then is able to view edge portions 30 and 32 by peering into crevice 34. Suture 12 may be colored to aid the surgeon in this manner. Suture 12 may be drawn through tissue 14 by suture needle 36 which may be of conventional construction. Suture needle 38, FIGS. 1–3, possesses a flexibility which permits the passage of the same through first suture 12. In the case where first suture 12 has collapsed at tissue portion 16, suture needle 38 possesses the capability of opening such a collapsed portion and passing through suture 12 without damage to the same. In this regard, suture needle 28 includes a blunted tip 40 which permits the cannulation of the same through suture 12, as hereinabove described.

Figure 3:
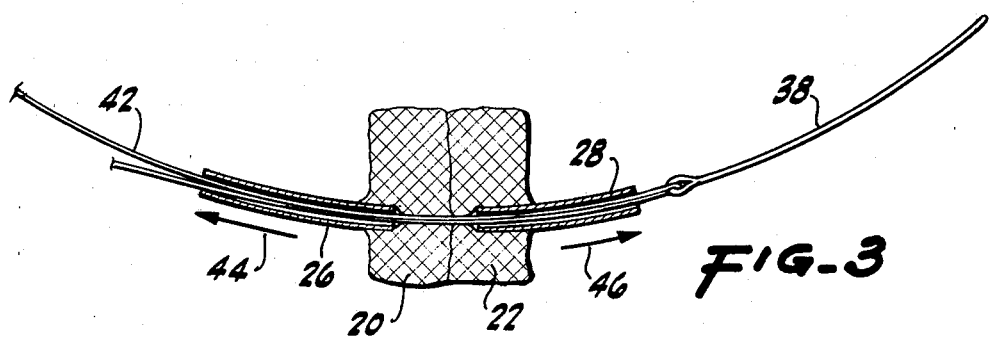
FIG. 3 is a broken sectional view showing the apparatus and method of the present invention in operation.
Figure 4:
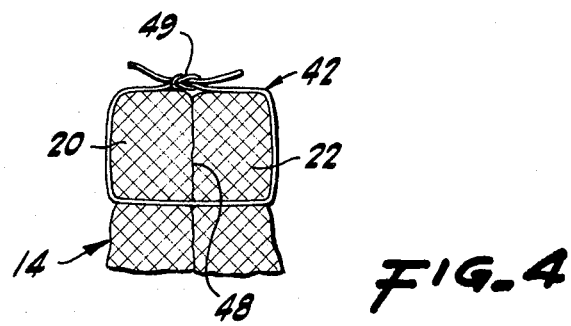
FIG. 4 is a broken sectional view showing the sutured severed portions of tissue.

Suture needle 38 draws a second suture 42 through first suture 12, more specifically portions 26 and 28 thereof, best shown in FIG. 2. Second suture 42 may be tied at this point to draw portions 20 and 22 of tissue together for healing. With reference to FIG. 3 it may be seen that sections 26 and 28 of first suture 12 may be drawn out of portions 20 and 22, arrows 44 and 46, such that second suture 42 remains within portions 20 and 22 exactly the same position as first suture 12, FIG. 1. Thus, portions 20 and 22 are very closely approximated or matched with reference to their position before the severing by surgical knife 18. In the case where a multiple stitch by suture 42 is desirable, a third suture having the same characteristics as first suture 12 (not shown) may be employed adjacent to first suture 12 along crevice 34. It may be apparent that the third suture or other sutures having the same characteristics as first suture 12 may be cut from portions 20 and 22 after the drawing of second suture 42 therethrough using suture needle 38 as a base or backing to prevent damage to second suture 42. With reference to FIG. 4, it may be seen that second suture 42 is tied with a knot 48 in the conventional manner. Injuncture 48 between sections 20 and 22 will readily heal as a result of the re-approximation of the portions 20 and 22 of tissue 14.

In operation, the method of suturing tissue 14 includes the steps of passing the first, flexible, tubular suture 12 through tissue 14. Surgical knife 18 is then employed to sever tissue 14 into portions 20 and 22 and first suture 12 into sections 26 and 28, FIG. 2. As heretofore described, the first suture 12 may collapse within tissue 14. A second suture 42 is passed through first suture 12 by the use of flexible suture needle 38 having a blunted tip 42. Collapsed portion 16 of first suture 12 may be reopened by this procedure simultaneously with the passage of second suture 42 through first suture 12. First suture portions 26 and 28, as well as any other portions if a multiplicity of first sutures are employed adjacent first suture 12 along crevice 38, may be removed along first suture 42 according to arrows 44 and 46, FIG. 3. Second suture 42 is fastened with knot 48 bringing sections 20 and 22 of tissue 14 together in very close re-approximation of their original positions in relation to one another before severing by surgical knife 18.

While in the foregoing embodiments of the present invention have been set forth in considerable detail for the purposes of making a complete disclosure of the invention, it may be apparent to those of skill in the art that numerous changes may be made in such details without departing from the spirit and principles of the invention.

What is claimed is:

1. A method of suturing severed tissue comprising:
   a. passing a first flexible, tubular suture through the tissue;
   b. collapsing at least a portion of said flexible, tubular suture;
   c. simultaneously opening said collapsed portion of said first, flexible, tubular suture and introducing a second suture through said first, flexible, tubular suture; and
   d. fastening said second suture in relation to the tissue.

2. The method of claim 1 which additionally comprises the step of severing said first, flexible, tubular suture after said step of collapsing at least a portion of said first, flexible, tubular suture.

3. The method of claim 2 which additionally comprises the step of removing said first, flexible, tubular suture from the tissue after said step of simultaneoulsy opening said collapsed portion of said first, flexible, tubular suture and introducing a second suture through said first, opened, flexible, tubular suture.

4. The method of claim 3 which additionally comprises the steps of:
   a. passing at least a third, flexible, tubular suture through the tissue adjacent the passing of said first, flexible, tubular suture;
   b. collapsing at least a portion of said second, flexible, tubular suture after said step of collapsing at least a portion of said first, flexible, tubular suture; and
   c. simultaneously opening said collapsed portion of said at least a third, flexible, tubular suture and introducing said second suture through said at least a third, opened, flexible, tubular suture after said step of simultaneously opening said collapsed portion of said first, flexible, tubular suture and, introducing a second suture through said first, opened, flexible, tubular suture.

5. A method of suturing tissue comprising:
   a. passing a first, flexible, tubular suture through the tissue;
   b. severing said first, flexible, tubular suture;
   c. introducing a second suture through said first, flexible, tubular suture; and
   d. fastening said second suture in relation to the tissue.

6. A kit for suturing tissue comprising:
   a. a first, flexible, severable, tubular suture being capable of passing through the tissue, said suture including at least one opening at one end portion of said suture;
   b. a flexible needle capable of entering said at least one opening and of passing through said first flexible, tubular suture, said flexible needle including means for expanding any collapsed portions of said flexible, severable, tubular, suture during said passage therethrough; and
   c. a second suture connected to said flexible needle and being capable of passage through said first flexible, severable, tubular suture with said flexible needle.

7. The suture apparatus of claim 6 in which said, flexible needle includes a blunted tip.

* * * * *